(12) United States Patent
Ring et al.

(10) Patent No.: US 6,534,490 B1
(45) Date of Patent: *Mar. 18, 2003

(54) UNSATURATED 14, 15-CYCLOPROPANOANDROSTANES, METHOD FOR THE PRODUCTION THEREOF AND PHARMACEUTICAL PREPARATIONS CONTAINING SAID COMPOUNDS

(75) Inventors: Sven Ring, Jena (DE); Sigfrid Schwarz, Jena (DE); Walter Elger, Berlin (DE); Birgitt Schneider, Jena (DE); Günter Kaufmann, Jena (DE); Lothar Sobek, Jena (DE)

(73) Assignee: Jenapharm GmbH & Co. KG., Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/720,135

(22) PCT Filed: Jun. 18, 1999

(86) PCT No.: PCT/DE99/01794

§ 371 (c)(1),
(2), (4) Date: Dec. 21, 2000

(87) PCT Pub. No.: WO99/67275

PCT Pub. Date: Dec. 29, 1999

(30) Foreign Application Priority Data

Jun. 22, 1998 (DE) .......................... 198 27 523

(51) Int. Cl.⁷ .......................... A61K 31/56; C07J 53/00; C07J 3/00; C07J 1/00

(52) U.S. Cl. .................. 514/182; 514/172; 514/173; 514/174; 552/508; 552/523; 552/525; 552/623; 552/610; 552/500

(58) Field of Search ................. 514/182, 172, 514/173, 174; 552/508, 523, 525, 623, 500, 610

(56) References Cited

U.S. PATENT DOCUMENTS

| | | | | |
|---|---|---|---|---|
| 3,007,945 A | | 11/1961 | Fried et al. ............... | 260/397.4 |
| 3,194,803 A | | 7/1965 | Bolton ................... | 260/239.57 |
| 3,262,949 A | | 7/1966 | Ringold et al. .......... | 260/397.3 |
| 3,624,111 A | | 11/1971 | Edwards .................. | 260/397.4 |
| 3,968,132 A | * | 7/1976 | Green et al. ............. | 260/397.3 |
| 4,100,027 A | | 7/1978 | Weber et al. ................ | 195/516 |

FOREIGN PATENT DOCUMENTS

EP      768 316      4/1997

* cited by examiner

*Primary Examiner*—Sabiha Qazi
(74) *Attorney, Agent, or Firm*—Millen, White, Zelano & Branigan, P.C.

(57) ABSTRACT

Described are new, unsaturated 14,15-cyclopropanoandrostanes of general formula (I) and their pharmaceutically acceptable salts, a process for their production and pharmaceutical preparations that contain these compounds. The compounds are characterized by hormonal (gestagenic and/or androgenic) activity and may be used for hormone replacement therapy.

6 Claims, No Drawings

UNSATURATED 14, 15-CYCLOPROPANOANDROSTANES, METHOD FOR THE PRODUCTION THEREOF AND PHARMACEUTICAL PREPARATIONS CONTAINING SAID COMPOUNDS

This application is a 371 of PCT/DE99/01794 filed on Jun. 18, 1999.

DESCRIPTION

The invention relates to new, unsaturated 14,15-cyclopropano-androstanes, their production and pharmaceutical preparations that contain these compounds.

Unsaturated 14,15-cyclopropano-androstanes of general formula I

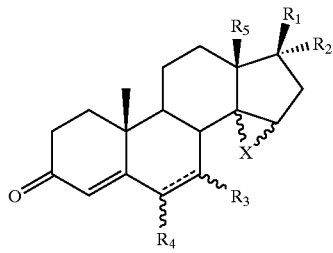

Formula I are described.

In general formula I, $R_1$ is a hydrogen atom, a hydroxy group, an alkyloxy, acyloxy, aryloxy, aralkyloxy or an alkylaryloxy group, a radical —OCONHR$_9$ or —OCOOR$_9$ with $R_9$ standing for a hydrogen atom, an alkyl, aryl, aralkyl or alkylaryl radical with 1–10 carbon atoms in each case, $R_2$ stands for a hydrogen atom, a hydroxyl group, an alkyl, acyl, aryl, aralkyl, alkylaryl group with 1–10 carbon atoms in each case, for a radical —(CH$_2$)$_n$CH$_2$Y with n=0, 1 or 2, and Y stands for a fluorine, chlorine, bromine or iodine atom, for a cyano, azido or rhodano group, for a radical —OR$_{10}$ or —SR$_{10}$ with R$_{10}$ standing for a hydrogen atom, an alkyl, aryl, aralkyl or alkylaryl radical with 1–10 carbon atoms in each case or an acyl radical COR9 with R$_9$ standing for an alkyl, aryl, aralkyl, or alkylaryl radical with 1–10 carbon atoms in each case, a radical —OR$_9$ with R$_9$ standing for a hydrogen atom, an alkyl, aryl, aralkyl or alkylaryl radical with 1–10 carbon atoms in each case, for a radical —(CH$_2$)$_m$—CH=CH(CH$_2$)$_n$—R$_8$ with m=0, 1, 2 or 3 and n=0, 1 or 2, and R$_8$ stands for a hydrogen atom, an alkyl, aryl, aralkyl or alkylaryl radical with 1–10 carbon atoms in each case or a hydroxyl group, an alkoxy group or acyloxy group with 1–10 carbon atoms in each case, a radical —(CH$_2$)$_o$C≡CR$_{11}$ with o=0, 1 or 2, and R$_{11}$ stands for a hydrogen atom, a fluorine, chlorine, bromine or iodine atom, an alkyl, aryl, aralkyl, alkylaryl or an acyl radical with 1–10 carbon atoms in each case, $R_1$ and $R_2$, independently of one another, stand for a keto, methylene, or difluoromethylene group, there can be a double bond between C-6 and C-7, an α- or β-cyclopropane group X, indicated by X, that is shown standing for a CZ$_2$ group with Z standing for a hydrogen, fluorine, chlorine, bromine or iodine atom, is located between C-14 and C-15, $R_3$ and $R_4$, independently of one another, stand for a hydrogen atom, an α- or β-position alkyl group with 1–10 carbon atoms, $R_5$ stands for an alkyl group with 1–3 carbon atoms.

The compounds according to the invention, the new, unsaturated 14,15-cyclopropano-androstanes, have not yet been described. Their biological action is still unknown.

The object of this invention is to make available unsaturated 14,15-cyclopropano-androstanes of general formula

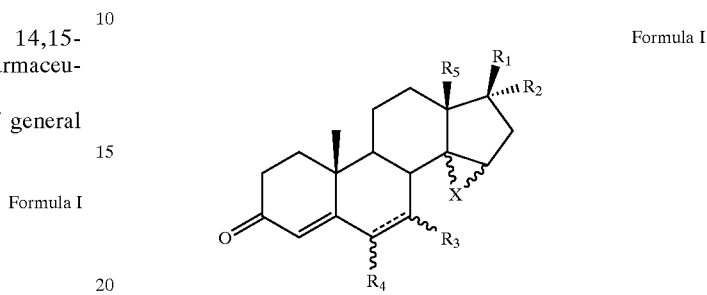

Formula I and their pharmaceutically acceptable salts as well as a process for their production.

Another object is to make available pharmaceutical preparations that contain at least one compound of general formula I or their pharmaceutically acceptable salts.

In general formula I

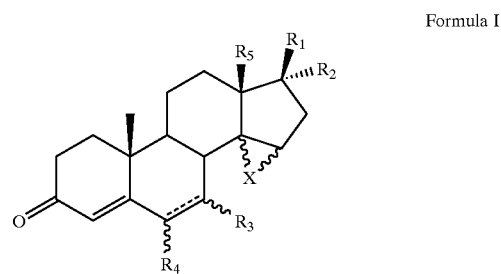

Formula I $R_1$ is a hydrogen atom, a hydroxy group, an alkyloxy, acyloxy, aryloxy, aralkyloxy or an alkylaryloxy group, a radical —OCONHR$_9$ or —OCOOR$_9$ with R$_9$ standing for a hydrogen atom, an alkyl, aryl, aralkyl or alkylaryl radical with 1–10 carbon atoms in each case, $R_2$ stands for a hydrogen atom, a hydroxyl group, an alkyl, acyl, aryl, aralkyl or alkylaryl group with 1–10 carbon atoms in each case, $R_2$ stands for a radical —(CH$_2$)$_n$CH$_2$Y with n 0, 1 or 2, and Y stands for a fluorine, chlorine, bromine or iodine atom, for a cyano, azido or rhodano group, for a radical —OR$_{10}$ or —SR$_{10}$ with R$_{10}$ standing for a hydrogen atom, an alkyl, aryl, aralkyl, or alkylaryl radical with 1–10 carbon atoms in each case or an acyl radical COR$_9$, with R$_9$ standing for an alkyl, aryl, aralkyl, or alkylaryl radical with 1–10 carbon atoms in each case, a radical —OR$_9$ with R$_9$ standing for a hydrogen atom, an alkyl, aryl, aralkyl or alkylaryl radical with 1–10 carbon atoms in each case, for a radical —(CH$_2$)$_m$—CH=CH(CH$_2$)$_n$—R$_8$ with m=0, 1, 2 or 3 and n=0, 1 or 2, and R$_8$ stands for a hydrogen atom, an alkyl, aryl, aralkyl or alkylaryl radical with 1–10 carbon atoms in each case or a hydroxyl group, an alkoxy group or acyloxy group with 1–10 carbon atoms in each case, a radical —(CH$_2$)$_o$C≡CR$_{11}$ with o=0, 1 or 2, and R$_{11}$ stands for a hydrogen atom, a fluorine, chlorine, bromine or iodine atom, an alkyl, aryl, aralkyl, alkylaryl or an acyl radical with 1–10 carbon atoms in each case, $R_1$ and $R_2$, independently of one another, stand for a keto, methylene, or difluoromethylene group, there can be a double bond between C-6 and C-7, an α- or β-cyclopropane group X, indicated by X, that is shown standing for a $CZ_2$ group with Z standing for a hydrogen, fluorine, chlorine, bromine or iodine atom, is located between C-14 and C-15, $R_3$ and $R_4$, independently of one another, stand for a hydrogen atom, an α- or β-position alkyl group with 1–10 carbon atoms, $R_5$ stands for an alkyl group with 1–3 carbon atoms. Most preferred are 17β-Hydroxy-14α,15α-methylen-androst-4-en-3-one (J 1193), 17α-hydroxy-14α,15α-methylen-androst-4-en-3-one, 17β-hydroxy-14β,15β-methylen-androst-4-en-3-one, 17α-hydroxy-14β,15β-methylen-androst-4-en-3-one, 17α-methyl,17β-hydroxy-14α,15α-methylen-androst-4-ene-3-one, 17β-methyl,17α-hydroxy-14α,15α-methylen-androst-4-en-3-one, 17α-methyl,17β-hydroxy-14β,15β-methylen-androst-4-en-3-one, 17β-methyl,17α-hydroxy-14β,15β-methylen-androst-4-en-3-one, 17β-hydroxy-6α-methyl-14α,15α-methylen-androst-4-en-3-one, 17α-hydroxy-6α-methyl-14α,15α-methylen-androst-4-en-3-one, 17β-hydroxy-6α-methyl-14β,15β-methylen-androst-4-en-3-one, 17α-hydroxy-6α-methyl-14β,15β-methylen-androst-4-en-3-one, 17β-hydroxy-7α-methyl-14α,15α-methylen-androst-4-en-3-one, 17α-hydroxy-7α-methyl-14α,15α-methylen-androst-4-en-3-one, 17β-hydroxy-7α-methyl-14β,15β-methylen-androst-4-en-3-one, 17α-hydroxy-7α-methyl-14β,15β-methylen-androst-4-en-3-one, 17β-hydroxy-14α,15α-methylen-androsta-4,6-dien-3-one, 17α-hydroxy-14α,15α-methylen-androsta-4,6-dien-3-one, 17β-hydroxy-14β,15β-methylen-androsta-4,6-dien-3-one, 17α-hydroxy-14β,15β-methylen-androsta-4,6-dien-3-one, 17α-methyl,17β-hydroxy-14α,15α-methylen-androsta-4,6-dien-3-one, 17β-methyl,17α-hydroxy-14α,15α-methylen-androsta-4,6-dien-3-one, 17α-methyl,17β-hydroxy-14β,15β-methylen-androsta-4,6-dien-3-one, 17β-methyl,17α-hydroxy-14β,15β-methylen-androsta-4,6-dien-3-one, 17β-hydroxy-7α,17α-dimethyl-14α,15α-methylen-androst-4-en-3-one, 17α-hydroxy-7α,17β-dimethyl-14α,15α-methylen-androst-4-en-3-one, 17β-hydroxy-7α,17α-dimethyl-14β,15β-methylen-androst-4-en-3-one, 17α-hydroxy-7α,17β-dimethyl-14β,15β-methylen-androst-4-en-3-one.

The invention also relates to a process for the production of the compounds according to general formula I and their pharmaceutically acceptable salts, which is characterized in that a compound of general formula II

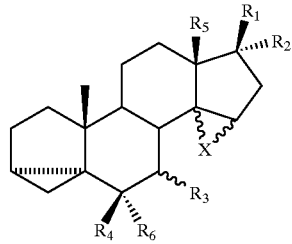

Formula II in which $R_1$, $R_2$, $R_3$ and $R_5$ have the above-indicated meaning, $R_4$ stands for a hydrogen atom, a hydroxy group, an alkoxyl group, an acyloxy group, an alkyl group with 1–10 carbon atoms in each case, $R_6$ stands for a hydrogen atom, a hydroxy group, an alkoxyl group, an acyloxy group, an alkyl group with 1–10 carbon atoms in each case, an α- or β-cyclopropane group X, indicated by X, that is shown representing a $CZ_2$ group, in which Z can mean a hydrogen, fluorine, chlorine, bromine or iodine atom, is located between carbon atoms 14 and 15, cleaves the 3,5-cyclopropane grouping with acids, whereby mineral acids, organic acids and Lewis acids are preferred, and then converts into the desired compounds of general formula I according to the methods that are known to one skilled in the art.

Subjects of this invention are pharmaceutical substances for oral, rectal, subcutaneous, intravenous or intramuscular use, which together with the commonly used vehicles and diluents can contain at least one compound of general formula I or its acid addition salts as an active ingredient.

Pharmaceutical preparations of the invention are produced with the commonly used solid or liquid vehicles and/or diluents and the generally commonly used adjuvants corresponding to the desired type of administration in a suitable dosage and in a way that is known in the art. In the case of a preferred oral form for dispensing, preferably tablets, film tablets, coated tablets, capsules, pills, powders, solutions or suspension are also prepared as a depot form.

In addition, parenteral dosage forms such as injection solutions or else suppositories are also considered.

Dosage forms as tablets can be obtained by, for example, mixing the active ingredient with known adjuvants, such as dextrose, sugar, sorbitol, mannitol, polyvinylpyrrolidone, explosives such as corn starch or alginic acid, binders such as starch or gelatin, lubricants such as magnesium stearate or talc and/or agents that can achieve a depot effect, such as carboxylpolymethylene, carboxymethylcellulose, cellulose acetate phthalate or polyvinyl acetate. The tablets can also consist of several layers.

Coated tablets can be prepared analogously by coating cores that are produced analogously to the tablets with agents that are commonly used in tablet coatings, for example polyvinylpyrrolidone or shellac, gum arabic, talc, titanium dioxide or sugar. In this case, the coated tablet shell can also consist of several layers, whereby for example, the above-mentioned adjuvants are used.

To improve the taste, the solutions or suspensions with the active ingredient according to the invention can be mixed with substances such as saccharin, cyclamate or sugar and/or with flavoring substances, such as vanillin or orange extract. In addition, they can be mixed with suspension adjuvants, such as sodium carboxymethyl cellulose or preservatives such as p-hydroxybenzoic acid.

The preparation of capsules can be carried out by mixing pharmaceutical substance with vehicles such as lactose or sorbitol, which then are introduced into the capsules.

The production of suppositories is preferably carried out by mixing the active ingredient with suitable vehicles, such as neutral fats or polyethylene glycols or derivatives thereof.

In addition, the pharmaceutical preparation forms can be percutaneous preparation forms, e.g., transdermal therapeutic systems (TTS) or gels, sprays or ointments or intranasal preparation forms such as nose spray or nose drops.

The unsaturated 14,15-cyclopropano-androstanes of general formula I according to the invention are hormonal (gestagenic-and/or androgenic-acting) compounds.

Thus, for example, the compound of general formula I, in which $R_1$ represents a hydroxyl group; $R_2$, $R_3$, $R_4$ represent a hydrogen atom; $R_5$ represents a methyl group; X represents a $CH_2$ group, and the 14,15-cyclopropane ring is in α-position, 17β-hydroxy-14α,15α-methylen-androst-4-en-3-one (J 1193), is an androgen.

While the substance 17β-hydroxy-14α,15α-methylen-androst-4-en-3-one (J 1193) with 24±3% binds to the androgen receptor of the rat prostate (reference substance: 17β-hydroxy-17α-methyl-estra-4,9,11-trien-3-one: R 1881), there is virtually no binding to the progesterone receptor of the rabbit uterus (reference substance: progesterone). In the Hershberger Test, a significant androgenic activity could be detected, however there is very little gestagenic action in the pregnancy maintenance test. The substance 17β-hydroxy-14α,15α-methylen-androst-4-en-3-one (J 1193) shows a pure androgenic profile of action that is almost free of gestagenic properties.

In the compounds of general formula I according to the invention, these test results open up many possibilities for birth control in men, hormone replacement therapy in men and women or the treatment of hormonally produced diseases in men and women, such as, for example, endometriosis, breast cancer or hypogonadism.

The compounds of general formula I according to the invention are to be explained in more detail in the examples below, but are not limited thereto.

EXAMPLE 1

17β-Hydroxy-14α,15α-methylen-androst-4-en-3-one 1 g of 17β-acetoxy-3,5-cyclo-6β-methoxy-14α,15α-methylen-androstane is dissolved in 50 ml of acetone, mixed with 0.1 ml of 60% perchloric acid and stirred for 40 minutes at 45° C. 20 ml of water is added, and then it is neutralized with sodium bicarbonate. The solvent is drawn off, the crystalline product is suctioned off and taken up in 200 ml of toluene. 50 ml of this solution is distilled off, then 150 mg of aluminum isopropylate and 2 ml of cyclohexanone are added, and it is heated for 40 minutes to 90° C. It is allowed to cool, acidified with 1N hydrochloric acid and worked up in extract form. The organic extract is concentrated by evaporation, and the residue is refluxed with 100 ml of 1N methanolic potassium hydroxide solution for 60 minutes. After cooling, it is neutralized with 1N hydrochloric acid, and the solvent is drawn off, whereby the product precipitates in solid form. The crystallizate is suctioned off and washed with water. The residue is chromatographed on silica gel (mobile solvent: toluene/ethyl acetate 10:2) and recrystallized from ethyl acetate.

Flash point: 167–172° C.; H-NMR: 0.13 (1H, dd, J=5.6, 3.2 Hz, $CH_2$-bridge), 0.24 (1H, dd, J=8.3, 5.6 Hz, $CH_2$-bridge), 1.01 (3H, s, H-18), 1.26 (3H, s H-19), 3.49 (1H, dd, J=9.4, 6.6 Hz, H-17), 5.71 (1H, s, H-4).

EXAMPLE 2

17β-Hydroxy-14β,15β-methylen-androst-4-en-3-one

The substance is produced from 17β-acetoxy-3,5-cyclo-6β-methoxy-14β,15β-methylen-androstane analogously to the instructions in Example 1.

Flash point 214–216° C.; H-NMR: 0.52 (1H, dd, J=8.3, 4.9 Hz, $CH_2$-bridge), 0.67 (1H, dd, J=4.9, 3.8 Hz, $CH_2$-bridge), 1.09 (3H, s, H-18), 1.20 (3H, s, H-19), 3.62 (1H, d, J=6.3 Hz, H-17), 5.71 (1H, s, H-4).

EXAMPLE 3

17β-Hydroxy-14β,15β-methylen-androsta-4,6-dien-3-one 1 g of 17β-hydroxy-14β,15β-methylen-androst-4-en-3-one (production, Example 2) is refluxed with 1.2 g of chloranil in 50 ml of tert-butanol for 30 minutes. It is allowed to cool and evaporated to the dry state. The residue is chromatographed on silica gel (mobile solvent: dichloromethane/ethyl acetate 10:1). For further purification, it is recrystallized from ethyl acetate.

Flash point 180–190° C.; H-NMR; 0.8 (2H, m, $CH_2$-bridge), 1.12 (3H, s, H-18), 1.13 (3H, s, H-19), 3.65 (1H, d, J=6.2 Hz, H-17), 5.67 (1H, s, H-4), 5.95 (2H, m, H-1, H-2).

EXAMPLE 4

17β-Hydroxy-7α-methyl-14β,15β-methylen-androst-4-en-3-one 80 ml of THF is added to a solution of methylmagnesium iodide (prepared from 2.5 g of magnesium and 6.4 ml of methyl iodide in 80 ml of diethyl ether), it is cooled to −5° C., and 1 g of copper acetate-monohydrate, dissolved in 50 ml of THF, is added. It is cooled to −20° C., and then a solution of 5 g of 17β-hydroxy-14β,15β-methylen-androsta-4,6-dien-3-one in 80 ml of THF is added in drops. After 2 hours, it is poured onto ice water/2N sulfuric acid and extracted with 3×80 ml of ethyl acetate. The organic extract is dried and concentrated by evaporation. The residue is chromatographed on silica gel (mobile solvent: dichloromethane/ethyl acetate 10:1). For further purification, it is recrystallized from ethyl acetate.

Flash point 140–145° C.; H-NMR: 0.59 (2H, m, $CH_2$-bridge), 1.02 (3H, d, J=8 Hz, H-7), 1.03 (3H, s, H-18), 1.12 (3H, s, H-19), 3.56 (1H, D, J=6 Hz, H-17), 5.68 (1H, m, H-4).

What is claimed is:

1. An unsaturated 14,15-cyclopropano-androstane of formula I

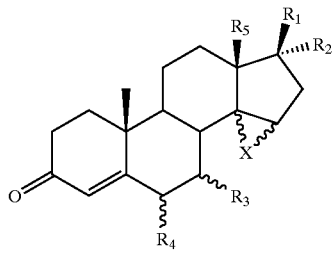

Formula I in which

R$_1$ is a hydrogen atom, a hydroxy group, an alkyloxy, acyloxy, aryloxy, aralkyloxy or an alkylaryloxy group, a radical —OCONHR$_9$ or —OCOOR$_9$
with R$_9$ standing for a hydrogen atom, or an alkyl, aryl, aralkyl or alkylaryl radical with 1–10 carbon atoms in each case, R$_2$ stands for a hydrogen atom, a hydroxy group, or an alkyl, acyl, aryl, aralkyl or alkylaryl group with 1–10 carbon atoms in each case,
for a radical —(CH$_2$)$_n$CH$_2$Y
wherein n=0, 1 or 2, and
Y stands for a fluorine, chlorine, bromine or iodine atom, or for a cyano, azido or rhodano group,
for a radical —OR$_{10}$ or —SR$_{10}$ with R$_{10}$
standing for a hydrogen atom, an alkyl, aryl, aralkyl, or alkylaryl radical with 1–10 carbon atoms in each case or an acyl radical COR$_9$,
with R$_9$ standing for an alkyl, aryl, aralkyl, or alkylaryl radical with 1–10 carbon atoms in each case,
for a radical —OR$_9$
with R$_9$ standing for a hydrogen atom, an alkyl, aryl, aralkyl or alkylaryl radical with 1–10 carbon atoms in each case,
for a radical —(CH$_2$)$_m$—CH=CH(CH$_2$)$_n$—R$_8$
wherein m=0, 1, 2 or 3 and n=0, 1 or 2,
and R$_8$ stands for a hydrogen atom, an alkyl, aryl, aralkyl or alkylaryl radical with 1–10 carbon atoms in each case, a hydroxyl group, or an alkoxy group or an acyloxy group with 1–10 carbon atoms in each case, or
for a radical —(CH$_2$)$_o$C≡CR$_{11}$
wherein o=0, 1 or 2, and R$_{11}$ stands for a hydrogen atom, a fluorine, chlorine, bromine or iodine atom, or an alkyl, aryl, aralkyl, alkylaryl or acyl radical with 1–10 carbon atoms in each case, or R$_1$ and R$_2$, independently of one another, stand for a keto, methylene, or difluoromethylene group, ==== means there can optionally be a double bond between C-6 and C-7, X stands for a CZ$_2$ group, with each Z standing independently for a hydrogen, fluorine, chlorine, bromine or iodine atom, and can be α- or β-X, R$_3$ and R$_4$, independently of one another, stand for a hydrogen atom, or an α- or β-position alkyl group with 1–10 carbon atoms, and R$_5$ stands for an alkyl group with 1–3 carbon atoms or a pharmaceutically acceptable salt thereof.

2. A compound according to claim 1, which is

17β-Hydroxy-14α,15α-methylen-androst-4-en-3-one,

17α-hydroxy-14α,15α-methylen-androst-4-en-3-one,

17β-hydroxy-14β,15β-methylen-androst-4-en-3-one,

17α-hydroxy-14β,15β-methylen-androst-4-en-3-one,

17α-methyl,17β-hydroxy-14α,15α-methylen-androst-4-ene-3-one,

17β-methyl,17α-hydroxy-14α,15α-methylen-androst-4-en-3-one,

17α-methyl,17β-hydroxy-14β,15β-methylen-androst-4-en-3-one,

17β-methyl,17α-hydroxy-14β,15β-methylen androst-4-en-3-one,

17β-hydroxy-6α-methyl-14α,15α-methylen-androst-4-en-3-one,

17α-hydroxy-6α-methyl-14α,15α-methylen-androst-4-en-3-one,

17β-hydroxy-6α-methyl-14β,15β-methylen-androst-4-en-3-one,

17α-hydroxy-6α-methyl-14β,15β-methylen-androst-4-en-3-one,

17β-hydroxy-7α-methyl-14α,15α-methylen-androst-4-en-3-one,

17α-hydroxy-7α-methyl-14α,15α-methylen-androst-4-en-3-one,

17β-hydroxy-7α-methyl-14β,15β-methylen-androst-4-en-3-one,

17α-hydroxy-7α-methyl-14β,15β-methylen-androst-4-en-3-one,

17β-hydroxy-14α,15α-methylen-androsta-4,6-dien-3-one,

17α-hydroxy-14α,15α-methylen-androsta-4,6-dien-3-one,

17β-hydroxy-14β,15β-methylen-androsta-4,6-dien-3-one,

17α-hydroxy-14β,15β-methylen-androsta-4,6-dien-3-one,

17α-methyl,17β-hydroxy-14α,15α-methylen-androsta-4,6-dien-3-one,

17β-methyl,17α-hydroxy-14α,15α-methylen-androsta-4,6-dien-3-one,

17α-methyl,17β-hydroxy-14β,15β-methylen-androsta-4,6-dien-3-one,

17β-methyl,17α-hydroxy-14β,15β-methylen-androsta-4,6-dien-3-one,

17β-hydroxy-7α,17α-dimethyl-14α,15α-methylen-androst-4-en-3-one,

17α-hydroxy-7α,17β-dimethyl-14α,15α-methylen-androst-4-en-3-one,

17β-hydroxy-7α,17α-dimethyl-14β,15β-methylen-androst-4-en-3-one, or

17α-hydroxy-7α,17β-dimethyl-14β,15β-methylen-androst-4-en-3-one.

3. A process for the production of a compound according to claim 1 comprising, in a compound of formula II,

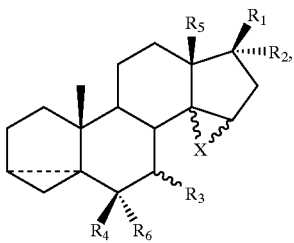

Formula II in which $R_1$, $R_2$, $R_3$, X and $R_5$ have the meaning that is indicated in claim 1, $R_4$ stands for a hydrogen atom, a hydroxy group, or an alkoxyl, acyloxy, or alkyl group with 1–10 carbon atoms in each case, and $R_6$ stands for a hydrogen atom, a hydroxy group, or an alkoxyl, acyloxy, or alkyl group with 1–10 carbon atoms in each case, cleaving the 3,5-cyclopropane group with an organic acid or a Lewis acid, and converting the product into a compound of formula I.

4. A pharmaceutical composition that comprises at least one compound of formula (I) according to claim 1 and a pharmaceutically acceptable carrier.

5. A method for birth control, hormone replacement therapy (HRT) or the treatment of a hormonally produced disease, comprising administering a compound of formula (I) according to claim 1.

6. A method of claim 5, wherein said disease is endometriosis, breast cancer or hypogonadism.

\* \* \* \* \*